United States Patent [19]
Fletcher et al.

[11] 4,092,633
[45] May 30, 1978

[54] CONDITION SENSOR SYSTEM AND METHOD

[76] Inventors: James C. Fletcher, Administrator of the National Aeronautics and Space Administration, with respect to an invention of John T. Polhemus, Englewood, Colo.; Joseph E. Morgan, Friendswood; Arthur Mandell, Seabrook, both of Tex.

[21] Appl. No.: 688,856

[22] Filed: May 21, 1976

[51] Int. Cl.² ............................................. G08B 21/00
[52] U.S. Cl. ................................ 340/213 R; 340/262; 340/279; 340/285; 340/309.1
[58] Field of Search ................ 340/58, 222, 261, 262, 340/279, 373, 213 R, 309.1; 324/178

[56] References Cited
U.S. PATENT DOCUMENTS

| 3,455,148 | 7/1969 | Foster et al. | 340/262 X |
| 3,811,116 | 5/1974 | Takeuchi et al. | 340/279 X |
| 4,031,527 | 6/1977 | Yanagishima et al. | 340/52 F X |

*Primary Examiner*—Alvin H. Waring
*Attorney, Agent, or Firm*—Marvin J. Marnock; John R. Manning; Marvin F. Matthews

[57] ABSTRACT

The condition sensor system comprises a condition detector which produces a pulse when a parameter of the monitored condition exceeds a desired threshold. A resettable condition counter counts each pulse. A resettable timer is preset to produce a particular time frame. The counter produces a condition signal when the accumulated number of pulses within the time frame is equal to or greater than a preset count. Control means responsive to the incoming pulses and to the condition signal produce control signals that control utilization devices. After a suitable delay, the last detected pulse simultaneously resets the pulse counter and the timer, and prepares them for sensing another condition occurrence within the time frame.

The invention has particular utility in the process of detecting rocking motions of blind people. A controlled, audible, bio-feedback signal is provided which constitutes a warning to the blind person that he is rocking. In addition, suitable tone signals can be recorded on a small recorder carried by the blind person. The tone signals are used for behavior analysis.

8 Claims, 4 Drawing Figures

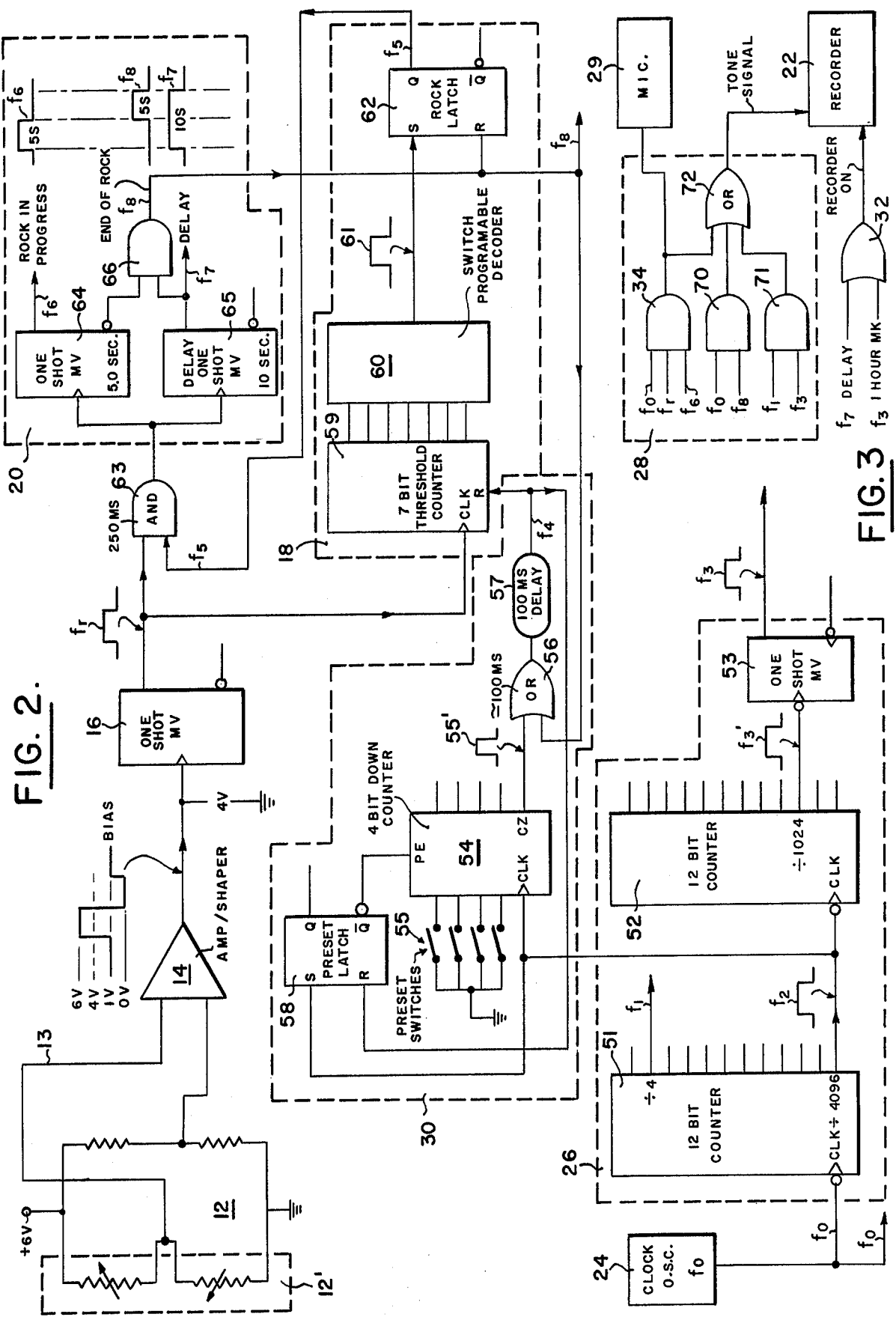

CONDITION SENSOR SYSTEM AND METHOD

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 45 U.S.C. 2457).

BACKGROUND OF THE INVENTION

This invention will be illustrated for monitoring the rocking motions of a blind person. Rocking motion is believed to be an unconscious and often an unwanted act exhibited by blind people. No system is presently available for detecting such rocking motions, for alerting the blind person, and for making a record of the frequency of the rocking motions. The record can be used for analysis by trained personnel.

Accordingly, it is a broad object of this invention to provide a condition sensor system suitable for sensing, analyzing, and recording various body conditions that can be sensed by transducers, accelerometers, optical sensors, etc., and which are susceptible of producing a number of occurrences within a specified time frame.

It is a more particular object of the invention to provide a rocking motion sensor (RMS) system for monitoring incidents of involuntary rocking in blind persons and to alert them thereof by means of an audible biofeedback signal.

SUMMARY OF THE INVENTION

The method using the condition sensor system can operate in three modes independently of each other or simultaneously. In the first or sensing mode, a counter counts pulses produced by a transducer and compares the accumulated count with a presettable timer to determine if a threshold has been reached within a time frame. When the preset time interval has elapsed and an insufficient number of pulses has been counted, the counter is automatically reset to zero and a new time frame is initiated. If within this time frame the number of counted pulses is greater than the preset number, then the threshold is exceeded and the system will produce timing control signals and an alert signal and will simultaneously shift into the second or feedback mode.

In the feedback mode the alert signal is a sensible means or indicia which is produced upon the occurrence of each monitored pulse. A recorder is turned on by a timing control signal for recording an indication corresponding to the alert signal. The system stays in the feedback mode until no further pulses are detected for a desired time interval after the last detected pulse, at which time a control signal will shift the system into the third or refractory mode.

During the refractory mode, a final signal is recorded, the recorder is turned off, and the system will shift back to the sensing mode.

When the events to be monitored are rockings by a blind person, the transducer can be an accelerometer which can be suitably mounted on a pair of eyeglasses, or other sensing means. The sensing means detects forces due to acceleration and gravity and is normally oriented to sense forward accelerations. Coupled to the transducer or other sensing means is a signal-conditioning amplifier which has a variable-gain adjustment that can be used to vary the rocking motion required to produce a rock signal. The overall system is preprogrammed to discriminate rocks from normal movements by varying three parameters: the amplitude of the motion required to produce a rock, the number of rocks required to reach a threshold, and the time frame during which the rocks are counted.

The system is timed by a clock which also produces tone signals for recording by the recorder. The various control signals are derived from multivibrators and suitable logic networks including AND and OR gates.

BRIEF DESCRIPTION OF THE DRAWINGS

FIG. 2 is a more detailed circuit of the system shown in FIG. 1;

FIG. 3 shows utilization networks coupled to the system shown in FIG. 2; and

DETAILED DESCRIPTION OF THE INVENTION

Figure 1:
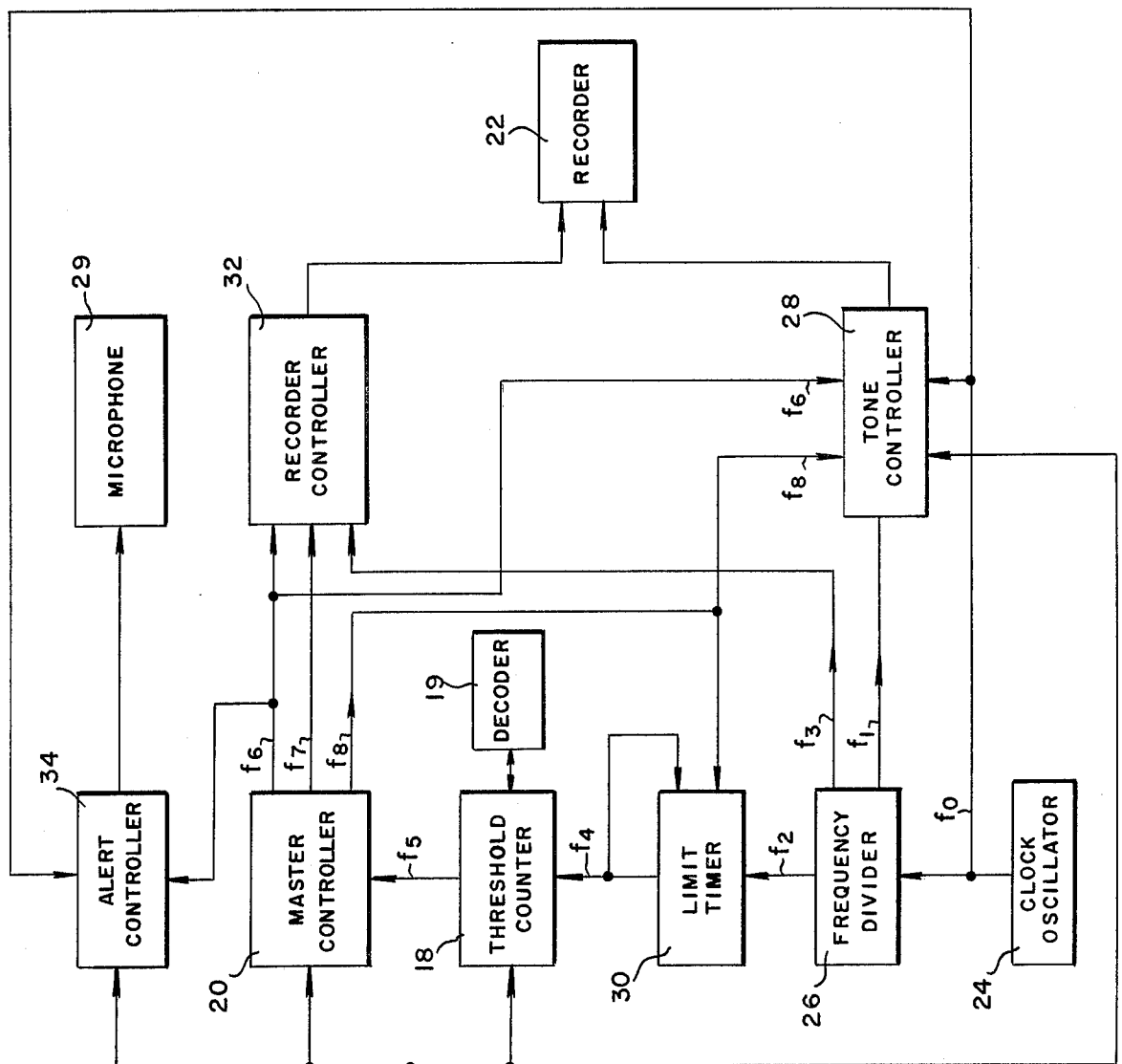
FIG. 1 is a block diagram of a rocking motion sensor system of this invention.

Referring now to FIG. 1, a suitable transducer 12, such as an accelerometer carried on the body of a blind person detects a rock motion and produces a corresponding electric signal which is fed over line 13 to an amplifier/shaper 14. The output signal from amplifier 14 has an amplitude proportional to the amplitude of the sway of the blind person. A rocking motion is said to occur if the amplitude of the pulse from amplifier/shaper 14 exceeds a threshold level sufficient to trigger a threshold detector 16. Each time that a rocking motion is detected, a rocking pulse $f_r$ will be produced by detector 16.

A clock oscillator 24 generates a clock signal $f_0$ which enters a frequency divider 26 producing distinct clock signals $f_1$, $f_2$, and $f_3$. Signal $f_1$ serves as an input to a tone controller 28. Signal $f_2$ serves as a clock input to a limit timer 30. Signal $f_3$ occurs once every hour and is applied to a recorder controller 32. Timer 30 can comprise a series of switches (not shown) which establish a preset number into a down counter (not shown). Clock $f_2$ decrements the preset number in the down counter until it reaches 0. At this time the counter produces an overflow signal $f_4$ which resets the counter to the preset number determined by its switch settings. This cycle is repetitive and each cycle produces a new time frame.

Overflow signal $f_4$ is also applied to a threshold counter 18 that receives $f_r$. A switch-programmable decoder 19 produces an event signal $f_5$ only after a predetermined count has been reached within the time frame produced by timer 30. Each time that a rocking motion or event occurs, as evidenced by the appearance of $f_r$, the number in counter 18 is incremented by one. Counter 18 must accumulate a number of rocking motions equal to or greater than the number set into the switch-programmable decoder 19. When the accumulated number of rocking motions is less than the number set into the decoder, the event signal $f_5$ does not occur and $f_4$ resets counter 18 to zero, thereby establishing a new count frame.

Signals $f_5$ and $f_r$ are inputs to a master controller 20. The arrival of $f_r$ is ignored by controller 20 until $f_5$ is detected. When the monitored event is a rocking motion, then rock is defined as a given number frame of such motions which occur within a given time frame, wherein each such motion produces a signal $f_r$. Master controller 20 generates control signals $f_6$, $f_7$ and $f_8$.

The first control signal $f_6$ is applied to an alert controller 34. Signal $f_6$ is also applied to a recorder controller 32 and to tone controller 28. The second control signal $f_7$ is applied to recorder controller 32 a predetermined time interval after $f_6$ falls to zero. Both signals $f_6$ and $f_7$ are reinitiated to their respective time durations, each time that a rocking motion signal $f_r$ occurs within the time span created by $f_6$. The third control signal $f_8$ sets timer 30 at the end of a rock, thereby closing a loop between timer 30 and master controller 20. The main functions of this loop are to monitor the number of rocking motions within the produced time frame.

The input signals to alert controller 34 are $f_r$, $f_6$ and $f_0$. After a rock has been detected, as evidenced by the arrival of $f_6$, clock $f_0$ is gated to a microphone 29 by the alert controller 34 each time that $f_r$ arrives within the time span created by $f_6$. The net result is the production of an audible beep by mic. 29, each time that a rock motion occurs after a rock has been detected.

Signals $f_3$, $f_6$, $f_7$ are inputs to recorder controller 32 which controls recorder 22. Signal $f_6$ turns the recorder on whenever a rock is detected, the recorder is held on by $f_7$ a given time interval after the end of $f_6$. Signal $f_3$ turns the recorder on for a desired time span in one hour increments.

Signals $f_1$, $f_0$, $f_6$, $f_8$ and $f_r$ are inputs to tone controller 28 which places a distinct tone on recorder 22 for each operative event. When a rock has been detected, signals $f_6$ and $f_r$ cause $f_0$ to be recorded as a short beep with the occurrence of each rocking motion. At the end of a rock, signal $f_8$ causes a strip of $f_0$ to be recorded as an end of rock tone. Signal $f_3$ causes signal $f_1$ to be recorded for 3 seconds as an hour mark.

The invention will be better understood with reference to the more detailed circuit diagram shown in FIG. 2, wherein the same reference characters are used to designate the same or similar blocks to facilitate the understanding of the invention. The invention will be described with reference to a presently preferred embodiment and a preferred mode of operation, but it should be understood that the invention is not limited thereto.

Transducer 12 is a four arm bridge having a pair of piezo-resistive accelerometers 12'. Bridge 12 can be easily mounted on a special pair of eyeglasses adapted for wear by a blind person being monitored. The accelerometer senses forces due to acceleration and gravity and is normally oriented to sense forward accelerations. The output of bridge 12 on line 13 is applied to a differential amplifier shaper 14 having an output DC bias of 1 volt. The output signal from amplifier 14 can range between 0 and 6 volts DC, depending on the amplitude of the swaying motion. The output of the amplifier is applied to a one-shot multivibrator (MV) 16 for producing a pulse $f_r$ having a duration of 250 ms when the output of amplifier 14 exceeds a threshhold level of 4 volts. Thus amplifier 14 amplifies and shifts the output signal of bridge 12 from bi-polar to uni-polar, and each time that a rocking motion is detected by bridge 12, a rocking pulse $f_r$ appears at the output of MV 16.

The clock oscillator 24 generates a 1165 Hz signal $f_0$ which enters divider 26 comprising a 12-bit counter 51 that divides $f_0$ by 4 to provide $f_1$ (291 Hz) and divides $f_0$ by 4,096 to provide $f_2$ which occurs once every 3½ seconds. Signal $f_2$ serves as the clock input to another 12-bit counter 52 that divides $f_2$ by 1,024 to produce $f_3$ which occurs once every hour. Signal $f_3$ triggers a one-shot multi-vibrator 53 which provides control signal $f_3$.

Limit timer 30 comprises a 4-bit down counter 54 provided with a series of manually-operated switches 55 that establish a preset time count into counter 54. Clock input $f_2$ sets a latch 58 and decrements this count to 0. At the 0 count, counter 54 produces a count-of-zero mark 55 of approximately 100 ms which is applied to an OR gate 56 that also receives the end-of-rock control signal $f_8$. The OR gate 56 is coupled to a 100 ms delay network 57 to produce overflow signal $f_4$ which is applied together with clock $f_2$ to latch 58. Signal $f_4$ resets the latch and presets counter 54 to the count determined by switches 55. A time frame having a range of 3½ to 52 seconds can be established by properly presetting switches 55 associated with the down counter 54 in timer 30.

Signals $f_r$ and $f_4$ serve as inputs to threshold counter 18 which comprises a 7-bit binary counter 59 coupled to a switch programmable decoder 60 that allows a pulse 61 to occur only after a threshold count has been reached. This count's limits are from 0 to 127 depending on the settings in decoder 60. Each time that a rocking motion occurs, as evidenced by the appearance of $f_r$, the count in counter 59 is incremented by 1. Counter 59 must count a number of rocking motions equal to or greater than the upper count limit programmed into decoder 60. When the number of rocking motions is less than the programmed count, rock pulse 61 does not appear and overflow signal $f_4$ resets counter 59 to 0, thereby establishing a new cycle. When the accumulated number of rocking motions is equal to or greater than the count set by decoder 60, pulse 61 appears and sets a rock latch 62 that produces a latch signal $f_5$.

Signals $f_5$ and $f_r$ are applied to a gate 63 which is coupled to a pair of retriggerable, one-shot, multi-vibrators 64, 65 connected in parallel. Multi-vibrator 64 produces the rock-in-progress pulse $f_6$ having a 5 second duration, and multi-vibrator 65 produces a delayed pulse $f_7$ having a 10 second duration. An AND gate 66 is coupled to multi-vibrators 65, 66 to produce end-of-rock pulse $f_8$ whenever pulse $f_6$ falls to a ZERO logic level. Thus output $f_7$ remains for 5 seconds after $f_6$ falls to ZERO.

It will be noted that both signals $f_6$ and $f_7$ are reinitiated to their respective time durations, each time that a rocking motion signal $f_r$ occurs within the 5 second time span created by $f_6$. End-of-rock signal $f_8$ resets the rock latch 62, thereby removing the latch signal $f_5$ from AND gate 63. Signal $f_8$ also passes through OR gate 56 and, after being delayed by delay 57, becomes $f_4$ which resets counter 59. Signal $f_4$ also resets latch 58 which presets counter 54.

With reference now to FIG. 3, signals $f_0$, $f_r$, and $f_6$ are applied to AND gate 34 which causes a small microphone 29 to reproduce clock signal $f_0$ when a rock is in progress, as evidenced by $f_6$, and for each subsequently detected rock motion, as evidenced by $f_r$. Signals $f_0$ and $f_8$ are applied to an AND gate 70. Signals $f_1$ and $f_3$ are applied to an AND gate 71. An OR gate 72 receives the output from AND gates 34, 70, 71 and provides the proper tone signal (either $f_1$ or $f_0$) to tape recorder 22. Signals $f_7$ and $f_3$ are applied to an OR gate 32 which turns on recorder 22.

In operation, after a rock has been detected, as evidenced by the arrival of $f_6$, clock $f_0$ is gated to mic. 29 each time that $f_r$ arrives within the 5 second time span created by $f_6$. Signal $f_6$ turns the recorder on whenever a rock has been detected. The recorder is held on by $f_7$ an additional 5 seconds after $f_6$ falls to ZERO. Signal $f_3$ turns on the recorder for 3 seconds each and every hour. The net result is that when a rock has been detected, signals $f_6$ and $f_r$ cause $f_0$ to be recorded as a short beep with the occurrence of each rocking motion. At the end of a rock, signal $f_8$ causes a strip of $f_0$ to be recorded as an end of rock tone. Signal $f_3$ causes a signal $f_1$ to be recorded for 3 seconds as an hour mark.

The system of this invention can operate in three modes independently of each other or simultaneously. In the first or sensing mode, counter 59 counts pulses $f_r$ produced by a transducer 12'. Decoder 60 compares the accumulated count with a threshold count to determine if a threshold has been reached within the time frame produced by counter 54. When the preset time interval has elapsed and an insufficient number of pulses has been counted by counter 59, counter 59 is reset to zero while a new time frame is initiated by counter 54. If within this time frame the number of counted pulses is greater than the preset number, then the threshold is exceeded and the system will produce rock signal $f_5$ and timing control signals $f_6$, $f_7$, and $f_8$ and will simultaneously shift into the second or feedback mode.

In the feedback mode signal $f_6$ starts an audible beep signal $f_0$ which is produced upon the occurrence of each monitored pulse $f_r$. Recorder 22 is turned on by $f_6$ for recording the beeps. The system stays in the feedback mode until no further $f_r$ pulses are detected for 5 sec. after the last detected pulse, at which time $f_8$ shifts the system into the third or refractory mode.

During the refractory mode, $f_0$ is recorded for 5 sec. at which time $f_7$ turns the recorder off, and the system will shift back to the sensing mode.

Figure 4:
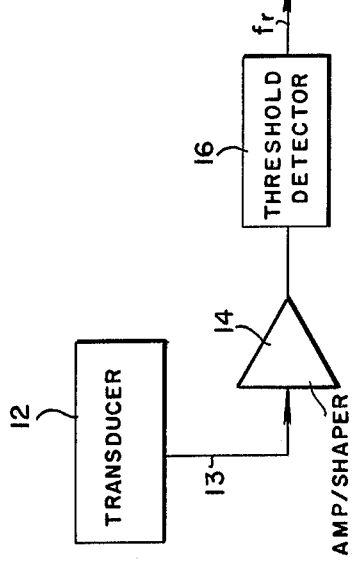
FIG. 4 shows the system mounted on a blind person.

Bridge 12 can be easily mounted on a pair of eyeglasses 80 (FIG. 4) for sensing forces dues to acceleration and gravity and is normally oriented to sense forward accelerations. Coupled to the transducer is a bio-belt 82 carried by the blind person. The bio-belt includes the signal-conditioning amplifier and the rest of the electronics together with tape recorder 22. Amplifier 14 has a variable-gain adjustment that can be used to vary the rocking motion required to produce a rock signal. The overall system is preprogrammed to discriminate rocks from normal movements by varying three parameters: the amplitude of the motion required to produce a rock (that is to trigger MV 16), the number of rocks required to reach a threshold count in counter 59, and the time frame established by counter 54 during which the rocks are counted.

The bio-belt provides an audio output to mic. 29 which is mounted in an ear plug 84 inserted in the ear of the blind person.

What is claimed is:

1. A sensor system for monitoring a variable condition, comprising:

a sensor coupled to the condition for producing a condition pulse whenever a parameter of the condition exceeds a threshold level, said sensor being coupled to a signal conditioner including a one-shot multi-vibrator and said multi-vibrator producing said pulse when the output of said signal conditioner exceeds a voltage corresponding to said threshold level;

a resettable limit counter counting each pulse produced by the sensor, a resettable timer establishing a time frame;

said counter producing a condition signal whenever, within said time frame, the count by said counter is equal to or greater than a threshold count;

control means responsive to said pulses and to said condition signal for producing control signals; and a utilization network controllable by said control signals.

2. The system of claim 1 wherein said sensor is an accelerometer.

3. The system of claim 2 wherein said accelerometer is a piezo-resistive bridge.

4. The system of claim 1 wherein said timer includes a down counter coupled to a plurality of switches which are adjustable to preset said time frame.

5. A sensor system for monitoring a variable condition, comprising:

a sensor coupled to the condition for producing a condition pulse whenever a parameter of the condition exceeds a threshold level;

a resettable limit counter counting each pulse produced by the sensor, a resettable timer establishing a time frame;

said counter producing a condition signal whenever, within said time frame, the count by said counter is equal to or greater than a threshold count;

control means responsive to said pulses and to said condition signal for producing control signals;

a utilization network controllable by said control signals, and said control means including a pair of retriggerable one-shot multi-vibrators, one of said multi-vibrators producing a first control pulse in response to said condition signal;

the other of said multi-vibrators producing:

a second control pulse starting with said first control pulse and ending a predetermined time interval thereafter, a third control pulse following the detection of the last condition pulse, and said third control pulse resetting said timer and said counter.

6. The system of claim 5 and further including a clock producing clock signals for clocking said timer.

7. The system of claim 5 and further including a recorder controllable by said control signals for recording tones indicative of the operation of said system.

8. The system of claim 5 and further including an alert device responsive to said first control signal.

* * * * *